US010280195B2

(12) United States Patent
Gagnon

(10) Patent No.: US 10,280,195 B2
(45) Date of Patent: May 7, 2019

(54) VIRUS REDUCTION METHOD

(71) Applicant: AGENCY FOR SCIENCE, TECHNOLOGY AND RESEARCH, Singapore (SG)

(72) Inventor: Peter Stanley Gagnon, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 124 days.

(21) Appl. No.: 15/313,363

(22) PCT Filed: May 28, 2014

(86) PCT No.: PCT/SG2014/000232
§ 371 (c)(1),
(2) Date: Nov. 22, 2016

(87) PCT Pub. No.: WO2015/183180
PCT Pub. Date: Dec. 3, 2015

(65) Prior Publication Data
US 2017/0158732 A1    Jun. 8, 2017

(51) Int. Cl.
*C07K 1/18*     (2006.01)
*B01D 15/16*    (2006.01)
*B01D 15/36*    (2006.01)
*B01J 20/28*    (2006.01)
*B01J 20/32*    (2006.01)
*B01J 41/04*    (2017.01)
*B01J 41/20*    (2006.01)
*B01D 15/42*    (2006.01)

(52) U.S. Cl.
CPC .............. *C07K 1/18* (2013.01); *B01D 15/168* (2013.01); *B01D 15/363* (2013.01); *B01J 20/3248* (2013.01); *B01J 41/04* (2013.01); *B01J 41/20* (2013.01); *B01D 15/428* (2013.01); *B01J 20/28016* (2013.01)

(58) Field of Classification Search
CPC . C07K 1/18; C07K 1/16; C07K 1/165; C07K 1/14; C07K 1/34; B01D 15/08; B01D 15/36; B01D 15/361; B01D 15/363; B01J 20/3242; B01J 20/3244; B01J 20/3246; B01J 20/28016; B01J 20/28033; B01J 20/28047; B01J 20/28042; B01J 41/04; B01J 41/07; B01J 41/08; B01J 41/20; B01J 47/14; B01J 47/15
See application file for complete search history.

(56) References Cited

U.S. PATENT DOCUMENTS

| | | | |
|---|---|---|---|
| 6,090,288 A | 7/2000 | Berglund et al. | |
| 6,783,929 B1 * | 8/2004 | Zuckermann | B01D 15/3804 210/600 |
| 7,001,550 B2 * | 2/2006 | van Reis | B01D 61/145 210/490 |
| 2009/0050566 A1 * | 2/2009 | Kozlov | B01D 15/1871 210/656 |
| 2010/0075131 A1 * | 3/2010 | Etzel | C08J 7/18 428/315.5 |
| 2010/0136025 A1 * | 6/2010 | Hickman | C07K 16/00 424/158.1 |
| 2010/0203650 A1 * | 8/2010 | Lowe | B01D 15/3804 436/501 |
| 2010/0234577 A1 * | 9/2010 | Mazzola | C07K 1/18 530/388.1 |
| 2011/0065900 A1 * | 3/2011 | Johansson | B01D 15/363 530/387.3 |
| 2011/0147292 A1 * | 6/2011 | Demmer | B01D 67/0093 210/198.2 |
| 2011/0210055 A1 * | 9/2011 | Srinivasan | B01J 39/26 210/198.2 |
| 2011/0217752 A1 * | 9/2011 | Rasmussen | C08G 69/10 435/183 |
| 2012/0077249 A1 * | 3/2012 | Ramaswamy | C12N 7/00 435/239 |
| 2013/0109807 A1 * | 5/2013 | Gagnon | C07K 16/065 525/54.1 |
| 2014/0005364 A1 * | 1/2014 | Gottschall | B01D 15/3804 530/387.3 |
| 2014/0301977 A1 * | 10/2014 | Nadarajah | B01D 15/14 424/85.2 |

FOREIGN PATENT DOCUMENTS

| | | |
|---|---|---|
| WO | WO 2013/062841 | 5/2013 |
| WO | WO 2013/180655 | 12/2013 |

OTHER PUBLICATIONS

Liu et al. Recovery and purification process development for monoclonal antibody production. mAbs 2:5, 480-499; Sep./Oct. 2010. (Year: 2010).*
Riordan et al., "Salt Tolerant Membrane Adsorbers for Robust Impurity Clearance", Biotechnol. Prog., 2009, vol. 25, No. 6, www.interscience.wiley.com., pp. 1695-1702.
Curtis, et al., "Generic/Matrix Evaluation of SV40 Clearance by Anion Exchange Chromatography in Flow-Through Mode", Biotechnology and Bioengineering, vol. 84, No. 2, Oct. 20, 2003, pp. 179-186.
Gagnon, "Technology Trends in Antibody Purification", Journal of Chromatography A, 1221 (2012), pp. 57-70.
Written Opinion dated Aug. 16, 2017, in related Singapore Patent Application No. 11201609908V.
International Search Report dated Aug. 26, 2014 in corresponding International Patent Application No. PCT/SG2014/000232 (5 pages).
Japan Intellectual Property Office, Office Action for Japanese Patent Application No. 2016-569418, Nov. 6, 2018, pp. 1-3.

* cited by examiner

*Primary Examiner* — Katherine Zalasky
(74) *Attorney, Agent, or Firm* — Pillsbury Winthrop Shaw Pittman, LLP

(57) ABSTRACT

Methods are provided for enhancing reduction of virus and viral DNA levels in protein preparations.

19 Claims, No Drawings

VIRUS REDUCTION METHOD

RELATED APPLICATIONS

This application is a U.S. National Stage of International Patent Application No. PCT/SG2014/000232, filed May 28, 2014, entitled Virus Reduction Method, and naming inventor Peter Stanley Gagnon, which published as International Patent Publication No. WO/2015/183180 on Dec. 3, 2015. The entire content of the foregoing application is incorporated herein by reference, including all text, tables and drawings.

BACKGROUND

Embodiments disclosed herein relate to methods for reduction of viruses and viral polynucleotides in preparations containing a desired protein to be purified.

Some virus species are known to be inactivated by means of exposure to extreme conditions such as highly acidic pH. These include most species of lipid-enveloped viruses. Some virus species are known to be resistant to such inactivation. These include many non-lipid enveloped virus species, also referred to as protein coat viruses.

Anion exchange chromatography is commonly used for the purification of proteins, including removal of contaminating virus species. Anion exchangers used for such applications are frequently quaternary amine ion exchangers. These applications are performed at neutral to slightly alkaline pH because they generally support the strongest virus binding under those conditions (C. Curtis et al, Biotechnol. Bioeng. 84 (2003) 179-185), and such conditions are required to remove contaminating host cell proteins in parallel with removing viruses (P. Gagnon, J. Chromatogr. A 1221 (2012) 57-70. Primary amine-based anion exchangers have also been described for removal of virus and host cell protein at neutral to alkaline operating pH (W. Riordan et al., Biotechnol. Prog. 25 (2009) 1695-1702).

SUMMARY

In some embodiments, disclosed herein are methods for reducing virus and viral DNA levels in an acidic preparation of a desired protein, the method comprising contacting the acidic preparation of the desired protein with a surface bearing a primary amine, secondary amine, or both.

DETAILED DESCRIPTION

Methods are provided for enhanced removal of virus and viral DNA from a preparation containing a desired protein, during or following low pH treatment, by contacting a low pH preparation with a solid surface bearing primary and/or secondary amines. As used herein, "low pH" treatment refers to a sufficiently low pH as part of a virus inactivation treatment, i.e., a sufficiently low pH to inactivate at least one virus. Thus, a top end of the pH range will typically not be greater than about 4.0. Thus, in some embodiments, a low pH may range, for example, from about 1.0 to about 4.0, in some embodiments, or from about 2.0 to about 4.0, or about from 2.0 to about 3.8. Those skilled in the art will appreciate that the pH may be selected to conform to regulatory standards. In a typical case, the upper end regulatory limit pH may be about 3.8. In some embodiments, there are provided methods for reducing virus and viral DNA levels in an acidic preparation of a desired protein, the method comprising contacting the acidic preparation of the desired protein with a surface bearing a primary amine, secondary amine, or both.

In some embodiments, an operating pH during the contacting step is in a range selected from the group consisting of (a) from about 2.0 to about 4.0, (b) from about 2.25 to about 3.75, (c) from about 2.5 to about 3.5, (d) from about 2.75 to about 3.25, (e) from about 3.5 to about 3.75, and (f) from about 3.25 to about 3.5 and intermediate ranges or intermediate individual values in between.

In some embodiments, a salt concentration during the contacting step is range selected from the group consisting of (a) from about 0.0, or a non-zero value, up to about 0.5M, (b) from about 0.05 to about 0.3M, and (c) from about 0.1 to about 0.2M. The salt concentration may be any intermediate ranges or intermediate individual values in between these recited ranges.

In some embodiments, the duration of the contacting step is in a range selected from the group consisting of (a) from about 15 to about 120 minutes, (b) from about 30 to about 60 minutes, (c) a non-zero amount less than about 30 minutes, (d) a non-zero amount less than about 15 minutes, (e) a non-zero amount less than about 10 minutes, (f) a non-zero amount less than about 5 minutes, (g) a non-zero amount less than about 2 minutes, (h) a non-zero amount less than about 1 minute, and (i) a time required to pass the preparation through a device housing the primary amine-bearing surface.

In some embodiments, the surface comprises one or more moieties selected from the group consisting of ethylenediamine, tris(2-aminoethyl)amine, diethylaminetriamine, triethylenetetraamine, tetraethylenepentamine, polyalkylamine. In some embodiments, the surface may comprise any primary amine, secondary amine, or combinations thereof. The surface may be derived from or take the form of any straight chain or branched primary monoamine fragment attached at the surface of a substrate. Exemplary primary amine moieties include, without limitation, fragments based on methylamine, ethylamine, propylamine, isopropylamine, butylamine, sec-butylamine, iso-butylamine, any isomeric configuration of hexylamine, any isomeric configuration of heptylamine, octylamines, any isomeric configuration of nonylamine, any isomeric configuration of decylamine, or mixtures or combinations thereof.

In some embodiments, diamine fragments may be employed. Suitable diamines include, without limitation, diamines of the general formula

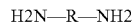

wherein R is linear or branched alkyl or alkenyl groups having about 1 and about 20 carbon atoms, cycloalkenyl groups having about 1 and about 20 carbon atoms, alkylcycloalkenyl groups having about 1 and about 20 carbon atoms, alkarenyl group having between about 1 and about 20 carbon atoms, aralkenyl group having about 1 and about 20 carbon atoms, or the like or mixtures or combinations thereof. The R group can also include atoms other than carbon and hydrogen such as oxygen, nitrogen, fluorine and/or chlorine.

Suitable surface amine moieties may be based on diamines and triamines including, without limitation, alkyl diamines, cycloalkyl diamines, alkacycloalkyl diamines, aralkyl diamines, aryl diamines, alkaryl diamines, and the like and analogs thereof and where one or more of the carbon atoms can be replaced with nitrogen atoms, oxygen atoms, or mixtures thereof where the oxygen atoms form carboxy, hydroxy and/or ether moieties and the nitrogen atoms form tertiary amine and/or amide moieties and/or one or more hydrogen atoms can be replaced with fluorine atoms, chlorine atoms or mixture thereof and including between 2 and about 20 carbon atoms, including, about 3 to about 15 carbon atoms and including, about 4 to about 10 carbon atoms. Exemplary alkyl diamines include, without limitation, 1,2-diaminoethane (1,2-ethylene diamine), 1,2-diaminopropane, 1,3-diaminopropane, 1,2-diaminobutane, 1,3-diaminobutane, 1,4-diaminobutane, 1,2-diaminopentane, 1,3-diaminopentane, 1,4-diaminopentane, 1,5-diaminopentane, and similar higher diaminoalkanes, hexamethylenediamine, aminomethylcyclopentylamine, 1,2-cyclopentanediamine, 1,6-hexanediamine, 1,2-diaminobenzene, lysine (or other diamine amino acids), 1,2-diaminobenzene, 1,4-diamine benzene, 1,2-diphenyl-1,2-ethane diamine, phenylene diamine, 2-hydroxypropylene diamine, hydantoin, N,N-Bis(dihydroxyethyl)ethylenediamine, hexahydrotriazine, aminoethylpiperazine (AEP) or the like, or mixtures or combinations thereof. Examples of other aliphatic diamines and triamines that are suitable for making the subject compositions include 1,4-diaminocyclohexane and bis-hexamethylenetriamine. In all of the aforementioned embodiments, presentation of the amine on the surface of a substrate may be achieved through connectivity to any atom of any of the fragments, including the nitrogen itself. In some embodiments, a secondary amine may also be employed. Such secondary amines may comprise a further straight chain or branched $C_1$ to $C_{20}$ fragment.

In some embodiments, the surface is in the form of one selected from the group consisting of a particle, a membrane, a monolith, a hydrogel-coated skeletal framework, and combinations thereof.

In some embodiments, the contacting step is performed by an operation selected from the group consisting of (a) dispersing primary and/or secondary amine-bearing particles in the preparation, (b) passing the preparation through a device in fluid contact with the surface, (c) recirculating the preparation through a device in providing fluid contact with the surface, and (d) combinations thereof.

It has been unexpectedly discovered that virus binding to primary and/or secondary amines on a solid surface breaks the accepted rules of anion exchange chromatography. Binding strength, as measured by the concentration of salt required to elute bound virus or viral polynucleotides from the primary amine-bearing surface, increases as a function of decreasing pH, in some cases by more than a factor of 2 compared to binding on the same surface at pH 8, by more than a factor of 5 compared to binding on quaternary exchangers at pH 8, and by nearly a factor of 10 compared to binding on quaternary exchangers at pH 6. Binding becomes progressively stronger at lower pH values so that at pH 3, up to 5 M guanidine is required to remove DNA from the primary and/or secondary amine-bearing surface. At the same time, experimental data show that retention of peptides and proteins with a mass lower than about 150 kDa is not enhanced compared to pH 8, thereby creating a window in which the desired protein in most preparations does not bind to the primary and/or secondary-amine-bearing surface under the conditions where retention of virus and viral DNA is enhanced. Experimental data show that this translates to a more than 700-fold reduction of non-lipid enveloped viruses such as Hepatitis A virus and Minute virus of Mice, which are not significantly inactivated by treatment with low pH. This is unexpected because retention of solutes such as viruses, DNA, and proteins on quaternary anion exchangers diminishes with decreasing pH, as a result of the solutes becoming more electropositive (and/or less electronegative).

This is generally understood to render anion exchange chromatography un-useful for virus removal at acidic pH, and especially at strongly acidic pH values, such as the conditions customarily used for virus inactivation. Without ascribing to any particular theory, the contrary behavior of viruses and viral DNA on primary and/or secondary-amine bearing surfaces may be mediated by hydrogen bonding. This is unexpected because hydrogen bonding is known to involve an electrostatic component that tends to suggest its contribution should parallel ion exchange behavior. Data from competition experiments with selective hydrogen donor-acceptors such as sorbitol nevertheless indicates hydrogen bonding. The behavior is further unexpected because it is distinct and contrary in multiple respects to results known in the art, indicating that retention increases substantially at pH 6 compared to pH 8 for proteins ranging in size from 18 to 78 kDa; indicating that there is no size correlation of increased binding with decreasing pH; and indicating that retention becomes strongest at about pH 6, weakens at lower pH, and is lost at pH 4-5 (U.S. Pat. No. 6,090,288). Supporting the methods disclosed herein, experimental data indicate that there is substantially no enhancement of retention for a protein of about 66 kDa, while there is a strong correlation between size and enhancement, and retention continues to become stronger at pH values below 6 for solutes with a size approaching about 1 MDa and greater, particularly at pH values less than 4, all of which are necessary enabling factors.

In some embodiments, the operating pH may be less than 6, such as pH 5 or less, or 4 or less, or 3.9 or less, or 3.8 or less, or 3.7 or less, or 3.6 or less, or 3.5 or less, or 3.4 or less, or 3.3 or less, or 3.3 or less, or 3.2 or less, or 3.1 or less, or 3.0 or less, down to the lowest pH that can be tolerated by the desired protein without it sustaining permanent damage that may affect its clinical efficacy or safety. In some embodiments, the tolerable pH may be 2.5 or less, or 2.0 or less, or about 1.0. The lowest tolerable pH will be understood to be unique to each desired product, and not possible to express on a broad generic basis. In some embodiments, the maximum pH will be no greater than about 4 since inactivation of even lipid-enveloped virus species requires a pH below 4. In some embodiments, the pH will between 3.25 and 3.75.

In some embodiments, the preparation may be devoid of salts. In some embodiments, the preparation may contain one or more species of salts, wherein the concentration of such salts is a non-zero amount up to 0.01M, up to 0.05M, up to 0.1M, up to 0.2M, up to 0.3M, up to 0.4M, up to 0.5M, or higher, potentially up to 1.0M. In some such embodiments, the species of salt may be sodium chloride (NaCl). In some embodiments, the presence of salt may have a negligible effect on virus removal by the primary amine-bearing surface, while in some embodiments the presence of salt may decrease the degree of virus removal achieved by the primary amine-bearing surface. In some embodiments, the presence of salts may either enhance virus inactivation, or improve stability of the desired protein, or decrease solubility of the desired proteins. Such effects can be determined for each species of desired protein. In some embodiments, increasing salt concentration within the indicated ranges may limit the degree to which virus removal is enhanced by the primary amine-bearing surface over the degree of inactivation achieved solely by treatment at low pH, but the degree of removal will remain significant.

In some embodiments, the preparation may contain elements intended to enhance virus inactivation, such as ethacridine, methylene blue, daunomycin, doxorubicin, chlorhexidine, alexidine, benzalkonium chloride, tris(2-aminoethyl)amine, tri(N-butyl)phosphate, a surfactant, a chelating agent, or combinations of such elements.

In some embodiments, the primary-amine-bearing surface may additionally include other species of electropositive chemical moieties, such as secondary amine groups. In other embodiments, the primary-amine-bearing surface may additionally include other species of electropositive chemical moieties, such as tertiary or quaternary amine groups. In some embodiments, the primary-amine bearing surface may additionally include more than one species of electropositive chemical moieties. In some embodiments, the primary-amine-bearing surface may additionally include a combination of electropositive chemical moieties consisting of secondary and tertiary amines; secondary and quaternary amines; tertiary and quaternary amines; secondary, tertiary, and quaternary amines, in any relative proportions.

In some embodiments, the chemical species that contains the primary amine, may be tris(2-aminoethyl)amine (TREN). In other embodiments, the chemical species that contains the primary amine may be ethylenediamine. In other embodiments the chemical species that contains the primary amine may be polyallylamine or another polymeric primary amine.

In some embodiments, the primary-amine-bearing surface may include chemical elements that permit the surface as a whole to engage in electrostatic interactions, hydrogen bonds, hydrophobic interactions, pi-pi bonding, and metal coordination interactions.

In some embodiments, the primary-amine-bearing surface may include elements with a charge opposite to the primary amines. In some embodiments, the primary-amine-bearing surface may include elements that are electroneutral, either by virtue of being uncharged or by virtue of containing balanced proportions of negative and positive charges, or both.

In some embodiments where a plurality of surfaces are present, the respective surfaces may bear the same primary amine-containing species. In some embodiments where a plurality of surfaces are present, the respective surfaces may bear different primary amine-containing species. In some embodiments where a plurality of surfaces are present, some of the respective surfaces may bear species other than primary amines.

In some embodiments, the primary-amine-bearing solid surface may be in the physical form of a particle, a membrane, a monolith, a hydrogel on a macro-reticulate skeleton. In some such embodiments, more than a single physical unit may be present, such as a plurality of particles, or a plurality of membranes, or a plurality of other physical forms, or combinations of different physical forms. In some such embodiments, a plurality of particles may be packed in a column.

In some embodiments, a plurality of primary-amine surfaces may be suspended within the preparation containing the desired protein. In some such embodiments, the suspended surfaces may be removed after treatment by sedimentation, or filtration, or flotation, or entrapment in a magnetic field, or entrapment on an oppositely charged surface, or any other expedient means. In some embodiments, the preparation containing the desired protein may be flowed through a device containing one or more primary-amine-bearing fluid-contact surfaces after low pH treatment for virus inactivation has been nominally completed. In some embodiments, the desired protein preparation may be recycled continuously through a device containing one or more primary-amine fluid contact surfaces for a period of time up to the full duration of the low pH treatment. In some embodiments, the desired protein preparation may be contacted with one or more primary amine binding surfaces by any combination of the foregoing modes of contact.

In one embodiment that illustrates the key elements of the disclosed method, a preparation containing a partially purified desired protein such as an IgG monoclonal antibody is titrated to a pH of 3.5 and held at that pH for 60 minutes. A monolith with a surface modified to bear ethylenediamine is equilibrated to nominally the same pH and salt conditions as the antibody preparation. The preparation is then flowed through the monolith. The monolith may optionally be rinsed with clean buffer at pH 3.5 to maximize recovery of the desired protein. The monolith may then optionally be discarded or regenerated.

In another embodiment that illustrates the key elements of the disclosed method, a preparation containing a partially purified antibody is titrated to a pH of 3.5. A monolith with a surface modified to bear ethylenediamine is equilibrated to nominally the same pH and salt conditions as the antibody preparation. The preparation is then recirculated through the monolith until the desired protein has been exposed to pH 3.5 for 60 minutes, or some other specified time interval.

In another embodiment that illustrates the key elements of the disclosed method, a preparation containing a partially purified antibody is titrated to a pH of 3.5. A membrane adsorber with a surface modified to bear polyallylamine is equilibrated to nominally the same pH and salt conditions as the antibody preparation. The preparation is then recirculated through the membrane for a period of 60 minutes. In a closely related embodiment, the antibody preparation is incubated at pH 3.5 for 60 minutes then flowed through the membrane adsorber in a single pass.

In another embodiment that illustrates the key elements of the disclosed method, a preparation containing a partially purified antibody is titrated to a pH of 3.5. Particles with surfaces modified to bear ethylenediamine, or polyallylamine, or other primary-amine-inclusive ligand are equilibrated to nominally the same pH and salt conditions as the antibody preparation. The particles are maintained in a suspended state by stirring for a period of 60 minutes, following which they are removed by sedimentation or filtration or any other expedient method. The particles may optionally be rinsed with clean buffer at pH 3.5 to maximize recovery of the desired protein. In a closely related embodiment, the antibody preparation is incubated at pH 3.5 for 60 minutes, then passed through a column packed with particles bearing ethylenediamine, polyallylamine, tris(2-aminoethyl)amine, or other primary-amine-inclusive ligand.

Terms below are defined so that the embodiments herein may be understood more readily. Additional definitions are set forth throughout the detailed description.

"Amines" are defined as organic compounds derived from ammonia by replacement of one or more hydrogen atoms with organic radicals, often with a hydrocarbon such as a methyl or ethyl group. On a "primary amine," one hydrogen atom is replaced by an organic radical. On a "secondary amine," two hydrogens are replaced by organic radicals. On a "tertiary amine," three hydrogens are replaced by organic radicals. On a "quaternary amine," three hydrogens are replaced by organic radicals and a fourth organic radical replaces an electron pair that exists on less substituted amines. Primary-amine-containing compounds may also contain other types of amines, or non-amine species.

"Hydrogen bonds" are defined as weak bonds between two molecules resulting in part from an electrostatic attraction between a proton in one molecule and an electronegative atom in another, and in part from covalent interactions.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope containing one or two layers of lipids. Examples include but are not limited to a dsDNA virus, a ssDNA virus, a dsRNA virus, a (+)ssRNA virus, a (−)ssRNA virus, a ssRNA RT virus and a dsDNA-RT virus; an adenovirus, a herpesvirus, a poxvirus, a parvovirus, a reovirus, a norovirus, a picornavirus, a togavirus, an orthomyxovirus, a rhabdovirus, a retrovirus, a hepadanvirus, a papillomavirus, a Human Immunodeficiency Virus (HIV), an influenza virus, dengue virus, Japanese encephalitis virus, West Nile virus, and bacteriophages. The term virus is understood to include virus particles for use as vectors for gene therapy, for use as vaccines, and as replacements for antibiotics. It is also understood to include so-called pseudovirions, which may be described as virus particles that have been recombinantly modified to conserve their ability to generate protective immunity while eliminating their ability to cause infection, and may also described as xenotropic viral species where distinct viral species spontaneously transfer genes from one to the other within a host that is infected with both.

"Virus inactivation" refers to a process that damages the virus in a way that suspends its ability to reproduce. Heat is commonly used for this purpose, as well exposure to chemical agents or extreme chemical environments such as highly acidic or highly alkaline conditions, or exposure to organic solvents, among others.

"Virus removal" refers to a process that removes virus from a preparation. Such removal may result from physical methods, such as filtration, where the porosity of a filtration device prevents the passage of virus, or size exclusion chromatography, where the size of a virus causes it to be fractionated from smaller proteins. Removal may also result from the chemical association of a virus with a complementary surface, such as a chromatography surface, such as in ion exchange, affinity, hydrophobic interaction, or hydroxyapatite chromatography, or other chromatography methods.

"Virus reduction" refers to the total reduction of virus load from a preparation by inactivation and removal.

"Viral polynucleotides" refers to the genetic material of a virus, in some case DNA, in some cases RNA.

In certain embodiments, the disclosed method can be applied without variation from the general examples described above to enhance virus reduction. The pH of the inactivating solution should be selected to achieve the highest degree of virus inactivation possible without consideration of the solid material bearing a primary amine. Within the effective range of pH values known to inactivate virus without permanently damaging the product of interest, which may be from a value lower than pH 4, to a value of about pH 3, the solid material may be expected to substantially enhance net viral reduction. Time of exposure may also be selected independent of the solid material bearing primary amine. Temperature of exposure may also be selected independent of the solid material bearing primary amine. Addition of antiviral components may be considered, however, it will be prudent to check certain variables to assess their individual and collective impact. Nonionic, zwitterionic, or positively charged additives can be expected to be tolerated without significant interference to the ability of the solid material bearing primary amines to retain virus or viral DNA. Electronegative additives may have a tendency to interfere with virus binding to the solid material bearing primary amines. Conductive additives such as salts may limit the ability of the solid material bearing primary amines to bind virus, though generally, salt concentrations that produce roughly physiological conductivity or less will be well tolerated, and in some embodiments, salt concentrations twice or thrice physiological conductivity will still permit the solid material bearing primary amines to deliver a worthy enhancement to overall virus reduction. Simple experiments can be conducted at various levels of additives to determine the degree to which they may reduce the ability of the solid material bearing primary amines to reduce virus. The technique known as Design of Experiments (DoE) is widely known in the art for minimizing the number of tests required to obtain a statistically valid body of data to identify the optimum conditions for a given set of variables. As a general matter, the conditions that support the most effective virus inactivation independent of the solid material bearing primary amines, will support the greatest overall reduction of virus in combination with the solid material bearing primary amines.

In some embodiments, the disclosed methods will enhance removal of DNA and/or contaminating proteins in parallel with enhancing virus reduction. Experimental data indicate that this occurs through the same chemical mechanism as virus reduction; unexpectedly increasing with decreasing pH. In some such embodiments, for example where the desired product does bind to the primary-amine-bearing surface, it may be advantageous to employ the lowest practical salt concentration to favor the highest reduction of virus. In other embodiments, for example where the desired protein has an attraction to the primary amine-bearing surface, it may be necessary to increase the salt concentration for the dual purpose of preventing loss of desired product, and to prevent bound desired protein from interfering with virus-binding capacity. In some such embodiments, the increase in salt concentration should generally not be greater than necessary to prevent desired protein loss and/or desired protein interference with virus binding. Since each species of desired protein presents different properties, it is understood that experimentation may be required to determine if salts are required, and to determine their minimum effective concentrations. It is within the ability of persons skilled in the art to determine the effective concentration through simple experiments.

In some embodiments, it will be beneficial to evaluate primary amine bearing surfaces and devices of various form and composition to determine which provides the most effective contact and highest capacity for virus reduction. As a general matter, membranes offer less flow resistance than monoliths but monoliths offer higher virus binding capacity. Porous particles suspended in the desired protein preparation generally suffer from poor capacity and retarded virus binding kinetics due to the large molecular distances among viruses and charged particles. Columns packed with porous particles offer more rapid kinetics than suspended particles, though they are still slow in comparison to membranes and monoliths and still suffer from low capacity, but porous particles may achieve worthy enhancement of virus reduction nonetheless.

EXAMPLES

Example 1

DNA binding on an ethylenediamine-bearing monolith (CIM EDA, BIA Separations) as a function of pH. Genomic DNA from salmon sperm was used as a surrogate for viral DNA. An EDA monolith was equilibrated with buffers ranging from pH 8.0 to 3.5 in separate experiments. DNA suspended in 50 mM Tris, pH 8 was injected onto the monolith. After a wash step to displace unbound sample components, the DNA was eluted in a linear gradient of either NaCl or guanidine. In both cases, results indicate a disproportionate increase in strength of retention beginning at pH 4. Experimental results are provided in Table 1:

TABLE 1

| pH | buffering species | M NaCl elution | M Guanidine elution |
|----|-------------------|----------------|---------------------|
| 8.0 | 50 mM Tris | 1.65 | 1.84 |
| 7.0 | 50 mM Hepes | 2.00 | 2.15 |
| 6.0 | 50 mM MES | 2.82 | 2.79 |
| 5.0 | 50 mM acetate | 3.35 | 3.06 |
| 4.0 | 50 mM acetate | 4.85 | 5.39 |
| 3.0 | 50 mM acetate | 4.85 | 5.41 |

Example 2

Enhancement of DNA retention on a primary amine-bearing surface versus weakened retention on a quaternary amine-bearing surface. Genomic DNA from salmon sperm was used as a surrogate for viral DNA. Retention of DNA was evaluated at pH 8, 7, and 6 on a primary amine-bearing monolith (CIM EDA, BIA Separations) versus a quaternary amine-bearing monolith (CIM QA, BIA Separations). DNA eluted from QA at 0.6M NaCl at pH 8.0, weakening to 0.55M NaCl at pH 7.0, and further weakening to 0.47M NaCl at pH 6.0. DNA eluted from EDA at 0.83M NaCl at pH 8.0, 1.11M NaCl, at pH 7.0, and 1.8M NaCl at pH 6.0. These results highlight the fact that retention on the primary amine-bearing surface is opposite to the trend, and of dramatically greater magnitude than observed with the quaternary amine-bearing surface.

Example 3

Enhancement of virus retention on a primary amine-bearing surface versus weakened retention on a quaternary amine-bearing surface. Bacteriophage M13 was used as a test virus. Retention of DNA was evaluated at pH 8, 7, and 6 on a primary amine-bearing monolith (CIM EDA, BIA Separations) versus a quaternary amine-bearing monolith (CIM QA, BIA Separations). DNA eluted from QA at 0.7M NaCl at pH 8.0, weakening to 0.61M NaCl at pH 7.0, and further weakening to 0.53M NaCl at pH 6.0. DNA eluted from EDA at 1.02M NaCl at pH 8.0, 1.47M NaCl, at pH 7.0, and 2.5M NaCl at pH 6.0. These results highlight the fact that retention on the primary amine-bearing surface is opposite to the trend, and dramatically greater than observed with the quaternary amine-bearing surface.

Example 4

Enhanced reduction of minute virus of mice (MVM) with a primary amine-bearing monolith. A viral cell culture containing MVM was exposed to pH 3.5 for 60 minutes. MVM is known not to be inactivated by these conditions. Solids were removed by filtration and the filtrate was passed through an EDA monolith equilibrated to pH 3.5. MVM content was reduced by a $\log_{10}$ factor of 2.85. This represents about a 700-fold enhancement of virus reduction, and particularly highlights the ability of the disclosed method to enhance removal of nonenveloped virus species, particularly including retroviral species such as MVM.

Example 5

Enhanced reduction of Hepatitis A virus (HAV) with a primary amine-bearing monolith. A viral cell culture containing HAV was exposed to pH 3.5 for 60 minutes. HAV is known not to be inactivated by these conditions. Solids were removed by filtration and the filtrate was passed through an EDA monolith equilibrated to pH 3.5. MVM content was reduced by a $\log_{10}$ factor of 2.85. This represents about a 700-fold enhancement of virus reduction and further highlights the ability of the disclosed method to enhance removal of nonenveloped virus species.

It will be apparent to the person of skill in the art, that the disclosed methods may also be used for the purification of viruses, especially non-lipid enveloped viruses where the low pH of binding may provide the secondary benefit of inactivating lipid-enveloped viruses in conjunction with purification. For the same reasons, it will be equally apparent that the disclosed methods may also be used for isolation of DNA from preparations that may be contaminated by lipid-enveloped viruses. In both cases, the ability of the disclosed methods to disproportionately enhance the retention of target products according to their size will also favor the elimination of smaller contaminants such as proteins.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present embodiments.

Many modifications and variations of the embodiments herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the embodiments being indicated by the following claims.

What is claimed is:

1. A method for reducing virus and viral DNA levels in an acidic preparation comprising a desired protein, the method comprising contacting the acidic preparation with an electropositive surface consisting essentially of one or more primary amines, secondary amines, or both, wherein an operating pH during the contacting step is from about 2.0 to about 4.0.

2. The method of claim 1, wherein the operating pH during the contacting step is in a range selected from the group consisting of (a) from about 2.25 to about 3.75, (b) from about 2.5 to about 3.5, (c) from about 2.75 to about 3.25, (d) from about 3.5 to about 3.75, and (e) from about 3.25 to about 3.5.

3. The method of claim 1, wherein a salt concentration during the contacting step is in a range selected from the group consisting of (a) from about 0.0 to about 0.5 M, (b) from about 0.05 to about 0.3 M, and (c) from about 0.1 to about 0.2M.

4. The method of claim 1, wherein the duration of the contacting step is in a range selected from the group consisting of (a) from about 15 to about 120 minutes, (b) from about 30 to about 60 minutes, (c) a non-zero amount less than about 30 minutes, (d) a non-zero amount less than about 15 minutes, (e) a non-zero amount less than about 10 minutes, (f) a non-zero amount less than about 5 minutes, (g) a non-zero amount less than about 2 minutes, (h) a non-zero amount less than about 1 minute, and (i) a time required to pass the preparation through a device housing the electropositive surface.

5. The method of claim 1, wherein the one or more primary or secondary amines are selected from the group consisting of ethylenediamine, tris(2-aminoethyl)amine, diethylaminetriamine, triethylenetetraamine, tetraethylenepentamine, and a polyallylamine.

6. The method of claim 1, wherein the electropositive surface is selected from the group consisting of a particle, a membrane, a monolith, and a hydrogel-coated skeletal framework.

7. The method of claim 1, wherein the contacting step is performed by an operation selected from the group consisting of (a) dispersing primary or secondary amine-bearing particles in the preparation, (b) passing the preparation through a device wherein the preparation is in fluid contact with the electropositive surface, and (c) recirculating the preparation through a device wherein the preparation is in fluid contact with the electropositive surface.

8. A method for reducing an amount of a virus in a preparation comprising a virus and a desired protein, the method comprising:
(i) contacting the preparation with an electropositive surface consisting essentially of one or more primary amines or secondary amines, wherein the preparation has a pH less than 4.0; and
(ii) separating the desired protein from the electropositive surface and the virus, wherein the electropositive surface comprises the virus.

9. The method of claim 8, wherein the preparation has a pH in a range from about 2.0 to about 3.75.

10. The method of claim 8, wherein a salt concentration of the preparation during the contacting step is from about 0.0 to about 0.5 M.

11. The method of claim 8, wherein the contacting step comprises a duration of about 15 to about 120 minutes.

12. The method of claim 8, wherein the one or more primary or secondary amines are selected from the group consisting of ethylenediamine, tris(2-aminoethyl)amine, diethylaminetriamine, triethylenetetraamine, tetraethylenepentamine, and polyallylamine.

13. The method of claim 8, wherein the electropositive surface consists essentially of one or more primary amines.

14. The method of claim 13, wherein the one or more primary amines consists of ethylenediamine.

15. The method of claim 8, wherein the electropositive surface comprises particles, a membrane, a monolith, or a hydrogel-coated skeletal framework.

16. The method of claim 8, wherein the contacting step is performed by an operation selected from the group consisting of (a) dispersing primary or secondary amine-bearing particles in the preparation, (b) passing the preparation through a device in fluid contact with the electropositive surface, and (c) recirculating the preparation through a device while providing contact of the preparation with the electropositive surface.

17. The method of claim 8, wherein the preparation comprises viral DNA and after the separating of (ii) the electropositive surface retains substantially all of the viral DNA.

18. The method of claim 8, wherein the preparation has a pH in a range from about 2.0 to about 3.75, and the electropositive surface comprises ethylenediamine.

19. The method of claim 8, wherein after (ii) the electropositive surface comprises substantially all of the virus.

* * * * *